United States Patent [19]

Belikan et al.

[11] Patent Number: 5,065,742
[45] Date of Patent: Nov. 19, 1991

[54] ULTRASONIC WAVE COUPLER FOR LOCATING TRANSDUCER IN A LITHOTRIPTIC APPARATUS

[75] Inventors: Thomas Belikan; Werner Krauss, both of Knittlingen, Fed. Rep. of Germany

[73] Assignee: Richard Wolf GmbH, Knittlingen, Fed. Rep. of Germany

[21] Appl. No.: 529,975

[22] Filed: May 29, 1990

[30] Foreign Application Priority Data

Jul. 10, 1989 [DE] Fed. Rep. of Germany ....... 3922641

[51] Int. Cl.⁵ ............................................. A61B 17/22
[52] U.S. Cl. ........................... 128/24 EL; 128/660.03; 73/644
[58] Field of Search ...................... 128/660.01, 660.03, 128/660.08, 660.09, 660.1, 662.03, 24 EL, 24 AA; 606/127-128; 73/644

[56] References Cited

U.S. PATENT DOCUMENTS

| | | | |
|---|---|---|---|
| 3,763,694 | 10/1973 | Rathburn et al. | 73/644 |
| 4,365,516 | 12/1982 | Moline | 73/644 |
| 4,387,720 | 6/1983 | Miller . | |
| 4,579,123 | 4/1986 | Chen et al. | 73/644 |
| 4,610,249 | 9/1986 | Makofski et al. | 128/24 EL |
| 4,722,346 | 2/1988 | Chen | 73/644 |
| 4,813,402 | 3/1989 | Reichenberger et al. | 128/24 EL |
| 4,821,730 | 4/1989 | Wurster et al. | 128/24 EL |
| 4,905,700 | 3/1990 | Wokalek et al. | 73/644 |

FOREIGN PATENT DOCUMENTS

| | | |
|---|---|---|
| 0234366 | 9/1987 | European Pat. Off. . |
| 0344773 | 12/1989 | European Pat. Off. . |
| 3737593 | 5/1988 | Fed. Rep. of Germany . |
| 2003701 | 3/1979 | United Kingdom . |
| 2009563 | 6/1979 | United Kingdom . |

*Primary Examiner*—Kyle L. Howell
*Assistant Examiner*—Scott R. Akers
*Attorney, Agent, or Firm*—Panitch, Schwarze, Jacobs & Nadel

[57] ABSTRACT

A diagnostic coupler is provided for transmitting ultrasonic waves from an ultrasonic locating transducer to a patient body, particularly for use in a lithotriptic apparatus having an ultrasonic shock wave transducer and at least one ultrasonic locating transducer. The coupler is a dimensionally stable body which is releasably arranged on the ultrasonic locating transducer by fitting to the shape of the ultrasound emitting end of the transducer. The material of the coupler has a characteritic wave impedance which is substantially the same as that of the patient body tissue.

11 Claims, 4 Drawing Sheets

ULTRASONIC WAVE COUPLER FOR LOCATING TRANSDUCER IN A LITHOTRIPTIC APPARATUS

FIELD OF THE INVENTION

This invention relates to a lithotriptic apparatus having an ultrasonic shockwave transducer and at least one ultrasonic locating transducer.

BACKGROUND OF THE INVENTION

It is known for an object, such as a concretion, which is going to be destroyed by means of a lithotriptic apparatus, to be located in the body of a patient undergoing treatment by using ultrasonic waves. What is used for this purpose is an ultrasonic locating transducer such as a B-scanner.

The standard to which location can be accomplished with an ultrasonic locating transducer is generally satisfactory, provided the sound head of the said transducer is resting directly against the skin of the patient. If however this is not the case, it becomes considerably more difficult to locate the object to be destroyed. Due to the occurrence of multiple echoes and, due to the poor acoustic matching between the surface of the skin and the surface of the sound head, many of the ultrasonic waves are reflected at the skin and thus fail to impinge on the sound head. As a result there is considerable degradation of the image obtained from the signals received by the ultrasonic locating transducer.

This problem is particularly prevalent in lithotriptic apparatus in which the ultrasonic locating transducer is positioned in the ultrasonic shockwave transducer. As illustrations, reference may be made to certain embodiments disclosed in DE-OS 35 43 867 (U.S. Pat. No. 4,821,730).

Because of the cone of shockwaves transmitted from the ultrasonic shockwave transducer, it is not possible for the sound head of the locating transducer to be moved up close to the focus of the shockwave transducer. If it were, it would screen-off too much of the shockwave energy. Consequently, what happens is that the quality of the locating image obtained is degraded, as outlined above, especially when it is surface structures such as gall stones or salivary concretions or tumors close to the surface which are being located. Also, the distance from the sound head of the locating transducer to the body of the patient depends on the patient's build. Hence this distance will be greater with children and slim persons than with corpulent patients.

Hence, against the background outlined above, the object of the invention is to provide a remedy for these disadvantages. Therefore, and in particular, the aim is to produce an arrangement which, in known lithotriptic apparatus, will always ensure good ultrasonic location in the patient's body of the object to be destroyed without at the same time screening off therapeutic ultrasonic shockwaves.

SUMMARY OF THE INVENTION

To this end, the present invention consists in a diagnostic coupling means for a lithotriptic apparatus having an ultrasonic shockwave transducer and at least one ultrasonic locating transducer, characterised in that it forms a dimensionally stable body which is releasably arranged on the ultrasonic locating transducer by fitting to the shape of the latter and which has a characteristic wave impedance substantially the same as that of body tissue.

The coupling means according to the invention can be fixed in place between the sound head of the locating transducer and the patient's skin. This bridges the gap between the sound head and the skin. Hence there are none of the multiple echos mentioned above. Because the characteristic wave impedance of the coupling means is substantially the same as that of body tissue, it is ensured that there will be excellent coupling of the ultrasonic waves emitted by the locating transducer into the patient's body. The connection between the locating transducer and the coupling means achieved by their shapes fitting to one another prevent any air-bubble inclusions from occuring, which would have an adverse effect on the quality of the locating image. What is more, due to the acoustic properties of the coupling means, ultrasonic shockwaves can pass through it largely unhindered.

The fit between the shapes of the coupling means and the locating transducer may advantageously be improved by forming the coupling means in the direction of the locating transducer, to be complementary to the surface geometry of the latter. This allows the ultrasonic waves to be coupled into the patient's body without losses.

Secure seating for the coupling means on the locating transducer can be obtained by having it overlap the transducer for some distance along its sides. Where the locating transducer is a B-scanner of conventional design, what this means is that the coupling means overlaps the body of the B-scanner by a substantial amount.

The mechanical strength of the coupling means can be increased by providing it with a fabric inlay in the region of its end which is seated on the locating transducer.

It is also possible for the security of seating on the locating transducer to be increased by strengthening the material of the coupling means in the region of its end which is seated on the locating transducer. This strengthening of the material may be of purely geometrical nature but another possibility envisaged is to strengthen it by exploiting an appropriate property of the material.

It is also possible for the coupling means to be fixed in place on the locating transducer by, as it were, strapping it in position with a collar, at its end which is seated on the locating transducer.

A material which is excellent for the coupling means is a hydrogel. In particular, the means may be composed of polyacrylamide agar gel, which has practically the same acoustic properties as water. The coupling means of polyacrylamide agar gel can be ideally applied to the patient's skin and the sound head of the locating transducer without any air being trapped, even without any additional coupling gel.

BRIEF DESCRIPTION OF THE DRAWINGS

In order that the invention may be more readily understood, some embodiments thereof will now be described, by way of example, with reference to the accompanying drawing, in which.

DESCRIPTION OF THE PREFERRED EMBODIMENTS

Figure 1:
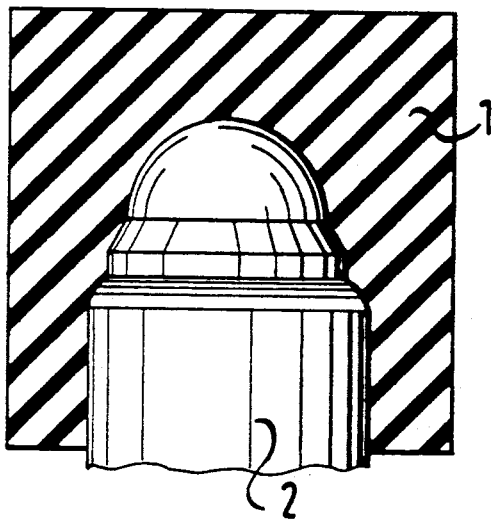
FIG. 1 shows an ultrasonic locating transducer with a diagnostic coupling means seated thereon.

Referring to FIG. 1, there is shown a coupling means 1 which is set up on an ultrasonic locating transducer 2. It can clearly be seen that the coupling means is seated on the locating transducer 2 by fitting to its form. The coupling means 1 forms a dimensionally stable body whose characteristic wave impedance is substantially the same as that of body tissue. In the embodiment shown in FIG. 1, the coupling means is formed, in the direction of the locating transducer 1, to be complementary to the surface geometry of the latter. This allows ultrasonic waves leaving the ultrasonic transducer 2 to be coupled into the patient's body without losses, i.e. without any air bubble inclusion.

Figure 2A:
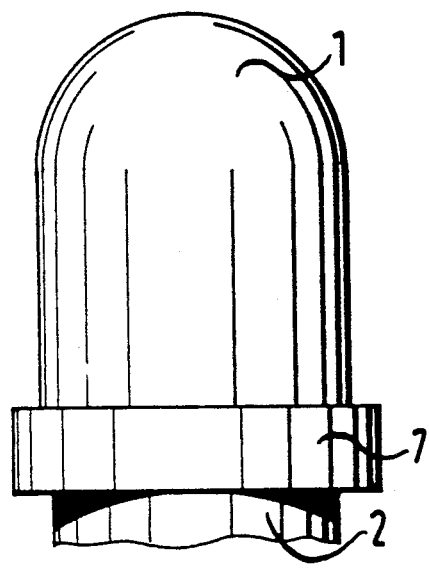
FIG. 2a is a side elevation of another coupling means which is secured in place on a locating transducer with a collar.

FIG. 2a shows a coupling means seated on the body of a locating transducer 2, the coupling means 1 being fastened in place on the locating transducer 2 by means of a collar 7 which fits round it. Details can be seen in FIG. 2b, which is a section through the item shown in side elevation in FIG. 2a. Also clearly apparent is the fact that the coupling means 1 overlaps the locating transducer 2 for a relatively long distance. At the end of the means which is sealed on the locating transducer 2 is provided a collar 7 by means of which the coupling means 1 is secured on the transducer 2.

Figure 3:
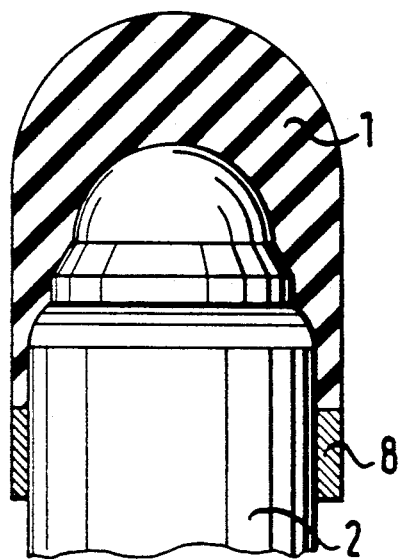

On the other hand, FIG. 3 shows how, in the embodiment illustrated, secure seating for the coupling means 1 on the locating transducer 2 is provided by means of a strengthening of the material in the region 8 of that end of the means which is seated on the transducer 2. If the coupling means 1 is composed of polyacrylamide agar gel for example the strengthening can be obtained by cross-linking the bottom rim of the coupling means to a considerably greater degree and thus making it relatively hard. Hardening of this kind can be achieved by altering the ratio of monomer to water.

Figure 2B:
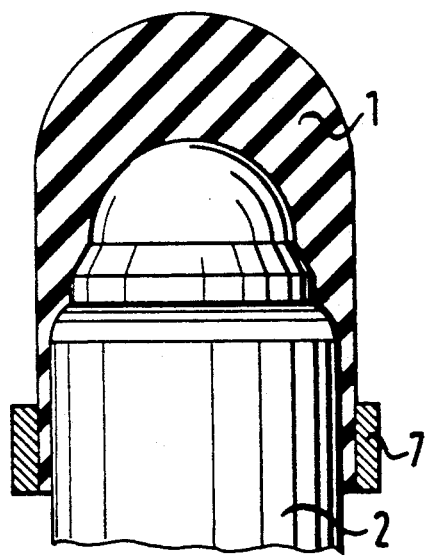
FIG. 2b is a section through the arrangement shown in FIG. 2a, FIG. 3 shows a coupling means on a locating transducer, the means being stably seated in position by means of a strengthening of its material.

Provisions as illustrated in FIGS. 2a, 2b and 3 will be useful in the majority of cases because, depending on its thickness and length, the center of gravity of the coupling means will be situated well above the locating transducer 2 and because in many cases the locating transducer 2, assuming it to be fitted in the ultrasonic shockwave transducer of the lithotriptic unit, will not normally be vertically positioned therein.

Figure 4:
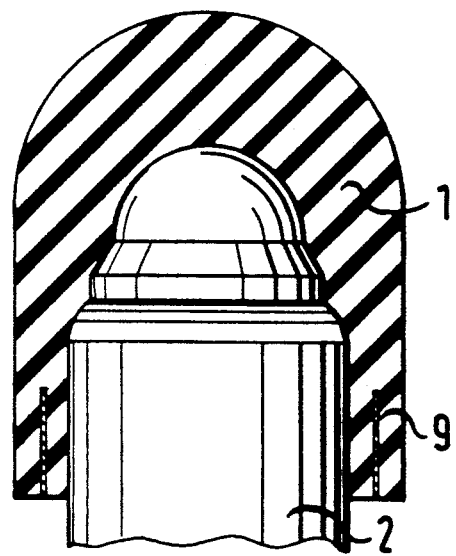
FIG. 4 shows a coupling means having a fabric inlay to increase its strength.

In FIG. 4 can be seen a coupling means 1 seated on a locating transducer 2 in which a fabric inlay 9 is incorporated in the region of the end of the means which is seated on the locating transducer 2. This fabric inlay 9 increases the strength of the coupling means and is thus also able to assist in providing a secure seating on the locating transducer 2.

Figure 5:
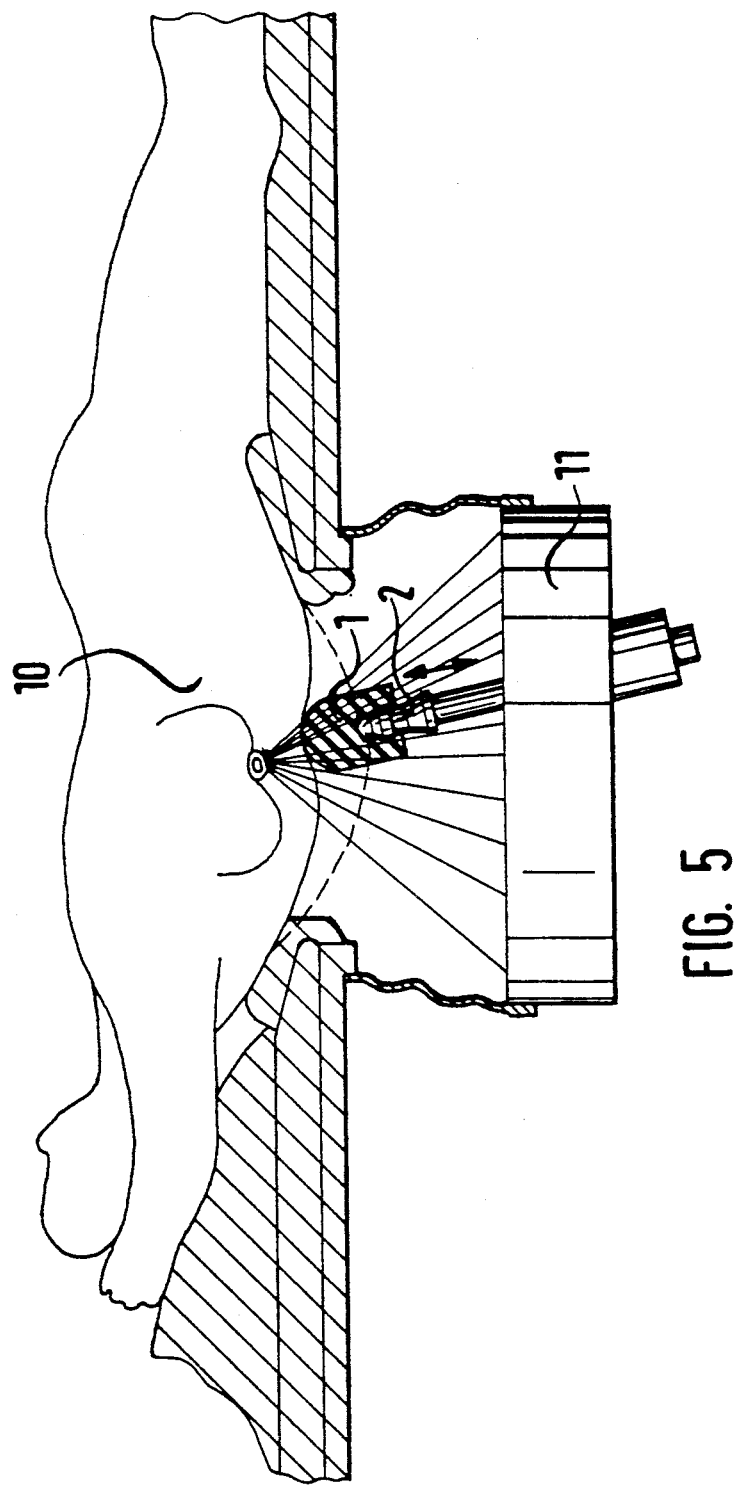
FIG. 5 is a diagram illustrating the use of a coupling means.

Referring to FIG. 5, this shows an embodiment of the coupling means 1. Installed in an ultrasonic shockwave transducer 11 of a lithotriptic apparatus is an ultrasonic locating transducer 2, the latter being so installed as to be displaceable in the direction of the double headed arrow. The coupling means is arranged on the locating transducer 2 in the manner described. It bridges the gap between the locating transducer 2 and the patient's body 10. Where the patient is corpulent (as indicated by the broken line), the distance between the sound head of the locating transducer 2 and the patient's skin is shorter than it is with a slim patient or a child. In extreme cases, the skin of the patient may be in direct contact with the sound head of the locating transducer 2, thus doing away with the need for the coupling means according to the invention to be interposed. This of course will only happen in very rare instances.

Whilst particular embodiments have been described, it should be appreciated that the invention is not limited thereto but includes all modifications and variations falling within the scope of the invention.

We claim:

1. A coupler for an ultrasonic locating transducer used in a lithotriptic apparatus, said coupler comprising a body having a first side which has a shape adapted to contact a patient's skin and a second side adapted to releasably fit the sound head of an ultrasonic locating transducer so as to allow ultrasonic waves from an ultrasonic locating transducer to be coupled into a patient without losses, said body consisting essentially of a material which is dimensionally stable and which has a characteristic wave impedance substantially the same as that of a patient's body tissue, and said coupler body further comprising means for securely and releasably seating the coupler on the ultrasonic locating transducer said coupler body and means for seating being constructed of one piece.

2. A coupler according to claim 1 wherein said second side is shaped to be complementary to the surface geometry of a sound head of an ultrasonic locating transducer so as to prevent air bubble inclusion between the coupler body and the sound head.

3. A coupler according to claim 1 wherein said seating means comprises an extension of said second side which is adapted to extend along the side of a locating transducer sufficiently far beyond the sound head of the transducer to ensure that the coupler will be securely seated thereon.

4. A coupler according to claim 3 wherein said extension has a fabric inlay to increase the strength of the material of the extension to provide secure seating.

5. A coupler according to claim 3 wherein a portion of the material of the extension is strengthened to increase the security of the seating.

6. A coupler according to claim 3 wherein said extension is provided with a collar to further ensure the secure seating of the coupler on an ultrasonic locating transducer.

7. A coupler according to claim 1 wherein said hydrogel is a hydrogel.

8. A coupler according to claim 7 wherein said hydrogel is a polyacrylamide agar gel.

9. A coupler according to claim 5 wherein said material is a polyacrylamide agar gel and the rim of the free end of said extension is strengthened by crosslinking the gel to a greater degree than the remainder of the coupler.

10. A coupler according to claim 1 wherein the material and shape of the coupler body are selected so as to prevent trapping of air between the coupler body and the sound head or the patient's skin without the need of any additional coupling gel.

11. A lithotriptic apparatus comprising a shock wave transducer and at least one ultrasonic locating transducer attached to the shock wave transducer and located therein, said locating transducer having a coupler releasably arranged thereon, said coupler comprising a body having a first side which has a shape adapted to contact a patient's skin and a second side adapted to releasably fit the sound head of the ultrasonic locating transducer so as to allow ultrasonic waves from the ultrasonic locating transducer to be coupled into a patient without losses, said body consisting essentially of a material which is dimensionally stable and which has a characteristic wave impedance substantially the same as that of a patient's body tissue, and said coupler body further comprising means for securely and releasably seating the coupler on the ultrasonic locating transducer said coupler body and means for seating being constructed of one piece.

* * * * *